United States Patent
Carballada et al.

(10) Patent No.: US 11,986,542 B2
(45) Date of Patent: *May 21, 2024

(54) COMPOSITION FOR ENHANCING HAIR FIBER PROPERTIES

(71) Applicant: The Procter & Gamble Company, Cincinnati, OH (US)

(72) Inventors: Jose Antonio Carballada, Cincinnati, OH (US); Lauren Elizabeth Ballhaus, Williamsburg, OH (US); Ron Walker, Pearland, TX (US); Jennifer Mary Marsh, Deerfield Township, OH (US); Supriya Punyani, Singapore (SG); Qing Stella, Cincinnati, OH (US); Curtis Bobby Motley, Hamilton, OH (US); Bernd Findeis, Sulzbach Gaunus (DE); Ingo Peter Herkert, Schwalbach (DE)

(73) Assignee: The Procter & Gamble Company, Cincinnati, OH (US)

( * ) Notice: Subject to any disclaimer, the term of this patent is extended or adjusted under 35 U.S.C. 154(b) by 325 days.

This patent is subject to a terminal disclaimer.

(21) Appl. No.: 17/410,531

(22) Filed: Aug. 24, 2021

(65) Prior Publication Data

US 2021/0386636 A1 Dec. 16, 2021

Related U.S. Application Data

(63) Continuation of application No. 16/359,627, filed on Mar. 20, 2019, now Pat. No. 11,129,780, which is a
(Continued)

(51) Int. Cl.
*A61K 8/36* (2006.01)
*A61K 8/34* (2006.01)
(Continued)

(52) U.S. Cl.
CPC ............ *A61K 8/361* (2013.01); *A61K 8/34* (2013.01); *A61K 8/36* (2013.01); *A61K 8/37* (2013.01);
(Continued)

(58) Field of Classification Search
CPC . A61K 8/34; A61K 8/36; A61K 8/361; A61K 8/37; A61K 8/732; A61K 8/891;
(Continued)

(56) References Cited

U.S. PATENT DOCUMENTS 3,798,317 A 3/1974 Gorum
4,330,438 A 5/1982 Dierassi et al.
(Continued)

FOREIGN PATENT DOCUMENTS

EP 0586764 A1 3/1994
EP 0908171 A1 4/1999
(Continued)

OTHER PUBLICATIONS

"Improved Revitalizing Conditioner", Mintel, Apr. 14, 2004, pp. 1-2.
(Continued)

*Primary Examiner* — Jeffrey T. Palenik
(74) *Attorney, Agent, or Firm* — John G. Powell; Alexandra S. Anoff

(57) ABSTRACT

Described herein is a hair care composition including from about 0.01% to about 20% of a lipid being one or more unsaturated fatty materials chosen from unsaturated fatty acids, unsaturated fatty alcohols, and mixtures thereof. The unsaturated fatty material has a Log P of less than 8. The hair care composition also includes from about 0.01% to about 10% of a fatty acid monoester of a polyol, a saturated fatty alcohol, an ester of a saturated fatty alcohol, and mixtures thereof. The molecule of the fatty acid component of the
(Continued)

fatty acid monoester includes a linear or a branched carbon chain with 10 to 22 carbon atoms. The fatty acid monoester of a polyol has a log P of less than 8. The molecule of the fatty alcohol includes a linear or branched carbon chain with 8 to 22 carbon atoms. The hair care composition also includes a non-aqueous volatile solvent.

17 Claims, 3 Drawing Sheets

Related U.S. Application Data continuation of application No. 15/416,045, filed on Jan. 26, 2017, now abandoned.

(60) Provisional application No. 62/288,853, filed on Jan. 29, 2016.

(51) Int. Cl.
| | | |
|---|---|---|
| A61K 8/37 | (2006.01) | |
| A61K 8/73 | (2006.01) | |
| A61K 8/891 | (2006.01) | |
| A61Q 5/00 | (2006.01) | |
| A61Q 5/12 | (2006.01) | |

(52) U.S. Cl.
CPC .............. *A61K 8/732* (2013.01); *A61K 8/891* (2013.01); *A61Q 5/002* (2013.01); *A61Q 5/12* (2013.01)

(58) Field of Classification Search
CPC ........ A61K 8/046; A61K 8/342; A61K 8/375; A61Q 5/002; A61Q 5/12
See application file for complete search history.

(56) References Cited

U.S. PATENT DOCUMENTS

| | | |
|---|---|---|
| 4,411,883 A | 10/1983 | Kenkare et al. |
| 4,450,151 A | 5/1984 | Shinozawa |
| 4,680,173 A | 7/1987 | Burger |
| 5,094,838 A | 3/1992 | Benson et al. |
| 5,246,694 A | 9/1993 | Birthwistle |
| 5,318,778 A | 6/1994 | Schmucker et al. |
| 5,605,682 A | 2/1997 | Ross et al. |
| 5,614,180 A | 3/1997 | Chung |
| 5,872,087 A | 2/1999 | Neelakantan |
| 5,939,082 A | 8/1999 | Oblong et al. |
| 5,977,036 A | 11/1999 | Gkey |
| 6,033,653 A | 3/2000 | Antoun |
| 6,040,282 A | 3/2000 | Guskey et al. |
| 6,106,849 A | 8/2000 | Malkan et al. |
| 6,156,298 A | 12/2000 | Karlen et al. |
| 6,177,390 B1 | 1/2001 | Guskey et al. |
| 6,200,554 B1 | 3/2001 | Yeoh et al. |
| 6,277,186 B1 | 8/2001 | Shi et al. |
| 6,287,546 B1 | 9/2001 | Reich et al. |
| 6,358,493 B1 | 3/2002 | Birkel et al. |
| 6,432,420 B2 | 8/2002 | Ellis et al. |
| 6,451,297 B1 | 9/2002 | Benoit et al. |
| 6,558,697 B2 | 5/2003 | Cannell et al. |
| 6,730,008 B1 | 5/2004 | Liang |
| 6,939,537 B2 | 9/2005 | Ohta et al. |
| 7,022,836 B2 | 4/2006 | Visser et al. |
| 7,150,868 B2 | 12/2006 | Ohta et al. |
| 7,157,076 B2 | 1/2007 | Pataut et al. |
| 7,237,697 B2 | 7/2007 | Dunne |
| 7,488,709 B2 | 2/2009 | Ribery et al. |
| 7,795,309 B2 | 9/2010 | Kisak et al. |
| 7,799,909 B2 | 9/2010 | Lewis |
| 7,854,947 B2 | 12/2010 | Cao et al. |
| 8,343,962 B2 | 1/2013 | Kisak et al. |
| 8,513,304 B2 | 8/2013 | Kisak et al. |
| 8,603,447 B2 | 12/2013 | Mueller et al. |
| 9,149,484 B2 | 10/2015 | Warner |
| 9,187,716 B2 | 11/2015 | Griffin et al. |
| 10,603,261 B2 | 3/2020 | Walker |
| 11,129,780 B2 | 9/2021 | Carballada et al. |
| 2001/0006621 A1 | 7/2001 | Coupe et al. |
| 2001/0006654 A1 | 7/2001 | Cannell et al. |
| 2003/0022799 A1 | 1/2003 | Alvarado et al. |
| 2003/0094104 A1 | 5/2003 | Jeffcoat et al. |
| 2003/0108649 A1 | 6/2003 | Jeffcoat et al. |
| 2003/0150885 A1 | 8/2003 | Dunne |
| 2003/0152533 A1 | 8/2003 | Tang |
| 2004/0131573 A1 | 7/2004 | Tang |
| 2004/0186030 A1 | 9/2004 | Hofrichter et al. |
| 2004/0247531 A1 | 12/2004 | Riedel et al. |
| 2005/0069511 A1 | 3/2005 | Magnet et al. |
| 2005/0095215 A1 | 5/2005 | Popp |
| 2005/0095261 A1 | 5/2005 | Popp |
| 2006/0029562 A1 | 2/2006 | Lane et al. |
| 2006/0029625 A1 | 2/2006 | Niebauer |
| 2006/0127345 A1 | 6/2006 | Hilvert et al. |
| 2006/0228319 A1 | 10/2006 | Vona et al. |
| 2006/0280714 A1 | 12/2006 | Maningat et al. |
| 2007/0184003 A1 | 8/2007 | Gaunitz |
| 2007/0292460 A1 | 12/2007 | Schiemann et al. |
| 2007/0297992 A1 | 12/2007 | Schiemann et al. |
| 2008/0095733 A1 | 4/2008 | Griffin et al. |
| 2008/0292575 A1 | 11/2008 | Uehara |
| 2009/0074697 A1 | 3/2009 | Huynh |
| 2009/0176676 A1 | 7/2009 | Hilvert et al. |
| 2009/0226381 A1 | 9/2009 | Maillefer et al. |
| 2009/0274642 A1 | 11/2009 | Dawson, Jr. |
| 2011/0048175 A1 | 3/2011 | LeVert |
| 2011/0168200 A1 | 7/2011 | Bourdin et al. |
| 2011/0174329 A1 | 7/2011 | Seng et al. |
| 2012/0084759 A1 | 4/2012 | Candea et al. |
| 2012/0104362 A1 | 5/2012 | Hanson et al. |
| 2012/0207693 A1 | 8/2012 | Mueller et al. |
| 2012/0213724 A1 | 8/2012 | Mueller et al. |
| 2012/0258052 A1 | 10/2012 | Mueller et al. |
| 2012/0282190 A1 | 11/2012 | Hammer |
| 2012/0328532 A1 | 12/2012 | Schweinsberg et al. |
| 2013/0116340 A1 | 5/2013 | Furukawa et al. |
| 2013/0243834 A1 | 9/2013 | Tanner |
| 2013/0267612 A1 | 10/2013 | Thiewes et al. |
| 2013/0302267 A1 | 11/2013 | Peffly et al. |
| 2013/0337031 A1 | 12/2013 | Kisak et al. |
| 2014/0000642 A1 | 1/2014 | Swaile et al. |
| 2014/0000643 A1 | 1/2014 | Swaile et al. |
| 2014/0030196 A1 | 1/2014 | Russell et al. |
| 2014/0155488 A1 | 6/2014 | Warner et al. |
| 2014/0335042 A1 | 11/2014 | Peffly |
| 2015/0297723 A1 | 10/2015 | Kisak et al. |
| 2016/0175209 A1 | 6/2016 | Walker et al. |
| 2017/0000718 A1 | 1/2017 | Swaile et al. |
| 2017/0000719 A1 | 1/2017 | Swaile et al. |
| 2017/0216172 A1 | 8/2017 | Carballada et al. |
| 2019/0282474 A1 | 9/2019 | Walker |

FOREIGN PATENT DOCUMENTS

| | | |
|---|---|---|
| JP | S59152308 A | 8/1984 |
| JP | S6416712 A | 1/1989 |
| JP | H0466525 A | 3/1992 |
| JP | 2528661 B2 | 1/1996 |
| JP | 2000500780 A | 1/2000 |
| JP | 2000143456 A | 5/2000 |
| JP | 200164126 A | 3/2001 |
| JP | 20011172129 A | 6/2001 |
| JP | 200287943 A | 3/2002 |
| JP | 3280328 B2 | 5/2002 |
| JP | 2005206573 A | 8/2005 |
| JP | 2006008610 A | 1/2006 |
| JP | 2007077057 A | 3/2007 |
| JP | 2008127337 A | 6/2008 |
| JP | 4589050 B2 | 9/2010 |
| JP | 2015101542 A | 6/2015 |
| JP | 2015124167 A | 7/2015 |
| WO | 9600563 A1 | 1/1996 |

(56) References Cited

FOREIGN PATENT DOCUMENTS

| WO | 9819652 | A1 | 5/1998 |
|---|---|---|---|
| WO | 9824402 | A1 | 6/1998 |
| WO | 200178661 | A2 | 4/2001 |
| WO | 0134103 | A1 | 5/2001 |
| WO | 03049711 | A2 | 6/2003 |
| WO | 2008080701 | A1 | 7/2008 |
| WO | 2009130714 | A2 | 10/2009 |
| WO | 2010086717 | A2 | 8/2010 |
| WO | 2011048175 | A1 | 4/2011 |

OTHER PUBLICATIONS

"Meta Velour Conditioner", Mintel Database, XP-002767701, database accession No. 1530012, dated Mar. 1, 2017, pp. 1-4.
14199MQ-DW PCT Search Report and Written Opinion for PCT/US2017/015017 dated Mar. 14, 2017, 10 pages.
All Office Actions; U.S. Appl. No. 15/416,045, filed on Jan. 26, 2017.
All Office Actions; U.S. Appl. No. 16/359,627, filed on Mar. 20, 2019.
Anonymous: "Dry-Flo TS Starch/Dry-Flo TS PURE Starch" Akzonobel Surface Chemistry; Personal Care, May 1, 2012, pp. 1-7.
Anonymous: "Firming Eye Treatment", Akzonobel Surface Chemistry; Global Personal Care, 2011, 2 pages.
Anonymous: "O/W Lightweight Sunscreen Lotion SPF 30+ (expected)", Akzonobel Surface Chemistry; Global Personal Care, XP-002726796, 2011, 2 pages.
Anonymous: "O/W Sunscreen Lotion SPF 30+ (Expected)", Akzonobel Surface Chemistry; Global Personal Care, XP-002726795, 2011, 2 pages.
Anonymous: "Reviving Dry Shampoo", Akzonobel Surface Chemistry; Global Personal Care, XP-002726794, 2011, 1 page.
Anonymous: "Silky Face Moisturizing Lotion", Akzonobel Surface Chemistry; Global Personal Care, XP-002726798, 2011, 2 pages.
Asada et al. "The newly elucidated mechanism of hair styling with the powder materials," Fragrance Journal 39 (6):40-46, 2011 (abstract only), 1 page.
Eiko Oshimura et al., J. Cosmet. Sci.; 58. published Jul./Aug. 2007, pp. 347-357.
International Cosmetic Ingredient Dictionary and Handbook, 10th Edition, 2004, "Hair Conditioning Agents.", pp. 2217-2227.
International Cosmetic Ingredient Dictionary and Handbook, 10th Edition, 2004, "Preservatives".
International Cosmetic Ingredient Dictionary and Handbook, 10th Edition, 2004, "Viscosity Increasing Agent", pp. 2293-2294.
McKay, Tonya: "The Science Behind Using Panthenol in Hair Products"; (www.curlynikki.com/2012/06/science-behind-using-panthenol-in-hair.html) published online Jun. 26, 2018.
Mintel; Conditioner; Unilever, Sep. 30, 2006.
Mintel; Reconstructing Conditioner, L'Oreal, Jun. 30, 2012.
Mintel; Reviving Conditioner, Private Label; Oct. 31, 2012, pp. 2-5.
Rohrschneider, Marc & Krenz, Holger, Aerosol Europe, vol. 13, Jan. 2005, pp. 6-11.
Tapioca Oil Absorption, Cosmetics and Toiletries Magazine, vol. 128, No. 8, Aug. 2013, p. 514.
XP002403573 Retrieved from the Internet: URL: http://web.archive.org/web/20041109220827/http://www.lindalgroup.com/documents/pdf/lindal_truspray.pdf . retrieved on Nov. 9, 2004, 3 pages.
"FIEDLER—Lexikon der Hilfsstoffe" [FIEDLER—Lexicon of Adjuvants], vol. 1, Fifth edition (2002), pp. 97-102.
Lee et al.; "Integral Lipid in Human Hair Follicle"; Journal of Investigative Dermatology Symposium Proceedings; vol. 10, Issue 3, dated Dec. 2005, pp. 234-237.
"Dry-Flo TS Starch: For Skin Care That Stands Out", Akzo Nobel Global Personal Care, 2004, pp. 1-2.

COMPOSITION FOR ENHANCING HAIR FIBER PROPERTIES

FIELD OF THE INVENTION

Described herein are hair care compositions comprising one or more materials useful for enhancing hair fiber properties.

BACKGROUND OF THE INVENTION

"Permanent" hair treatments, such as coloring, bleaching and straightening/waving, as well as other environmental and consumer habits (UV light, thermal drying, brushing/combing) cause damaged hair in various ways. Typically, hair damage also leads to the loss of natural internal lipids (as well as hair protein), which play an important role in hair structure. For example, lipids hold the hair proteins together as part of the cuticle/cortex membrane. Thus, internal hair lipid loss is associated with reduced hair mechanical strength. Loss of lipids also leads to increased moisture uptake when the hair is exposed to high humidity, leading to frizz. The present invention is directed to the development of compositions that can replenish internal lipids and repair damaged hair fibers.

Consumers using compositions of this technology experience an improvement in hair health from penetration of these materials and blends, resulting in more softness and combability. Consumers' hair becomes more structurally similar to emerging hair in terms of the internal lipid content. Typical current commercial hair care products contain surface benefit agents such as silicones and deposition polymers, to aid in lowering the surface energy of hair to protect against mechanical damage from combing. However, the use of typical commercial products do not significantly prevent hair tip damage, because of damage of the internal hair structure likely caused from loss of hair lipids and proteins through washing, UV and coloring damage. The present invention seeks to improve fiber properties by introducing lipids inside the hair fiber. Consequently, a need exists for a product that replenishes internal hair lipids providing improved softness and combability.

SUMMARY OF THE INVENTION

Described herein is, in an embodiment, a hair care composition comprising (a) from about 0.01% to about 20% of a lipid being one or more unsaturated fatty materials, by weight of the hair care composition, selected from the group consisting of unsaturated fatty acids, unsaturated fatty alcohols, and mixtures thereof; wherein the unsaturated fatty material comprises a linear or branched carbon chain with 8 to 24 carbon atoms and one carbon-carbon double bond between position C3 and position omega for the unsaturated fatty acid and between position C2 and position omega for the unsaturated fatty alcohol; and wherein the unsaturated fatty material has a Log P of less than 8; (b) from about 0.01% to about 10%, of one or more lipid enhancing agents, by weight of the hair care composition, selected from the group consisting of (i) a fatty acid monoester of a polyol wherein the molecule of the fatty acid component of the fatty acid monoester comprises a linear or branched carbon chain with 10 to 22 carbon atoms and wherein the fatty acid monoester of a polyol has a Log P of less than 8; (ii) a saturated fatty alcohol wherein the molecule of the fatty alcohol comprises a linear or branched carbon chain with 8 to 22 carbon atoms; (iii) an ester of a saturated fatty alcohol wherein the molecule of the ester comprises 10 to 44 total carbon atoms; and (iv) mixtures thereof; and (c) a non-aqueous volatile solvent.

Also described herein is, in an embodiment, a hair care composition comprising (a) from about 0.1% to about 5% oleic acid, by weight of the hair care composition; (b) from about 0.01% to about 5% glycerol monooleate, by weight of the hair care composition; wherein the weight ratio of oleic acid to glycerol monooleate is from about 1:1 to about 10:1; (c) from about 10% to about 75% of ethanol, by weight of the hair care composition; and (d) from about 25% to about 70% of a compressed propellant, by weight of the hair care composition.

DETAILED DESCRIPTION OF EMBODIMENTS OF THE INVENTION

Figure 1:
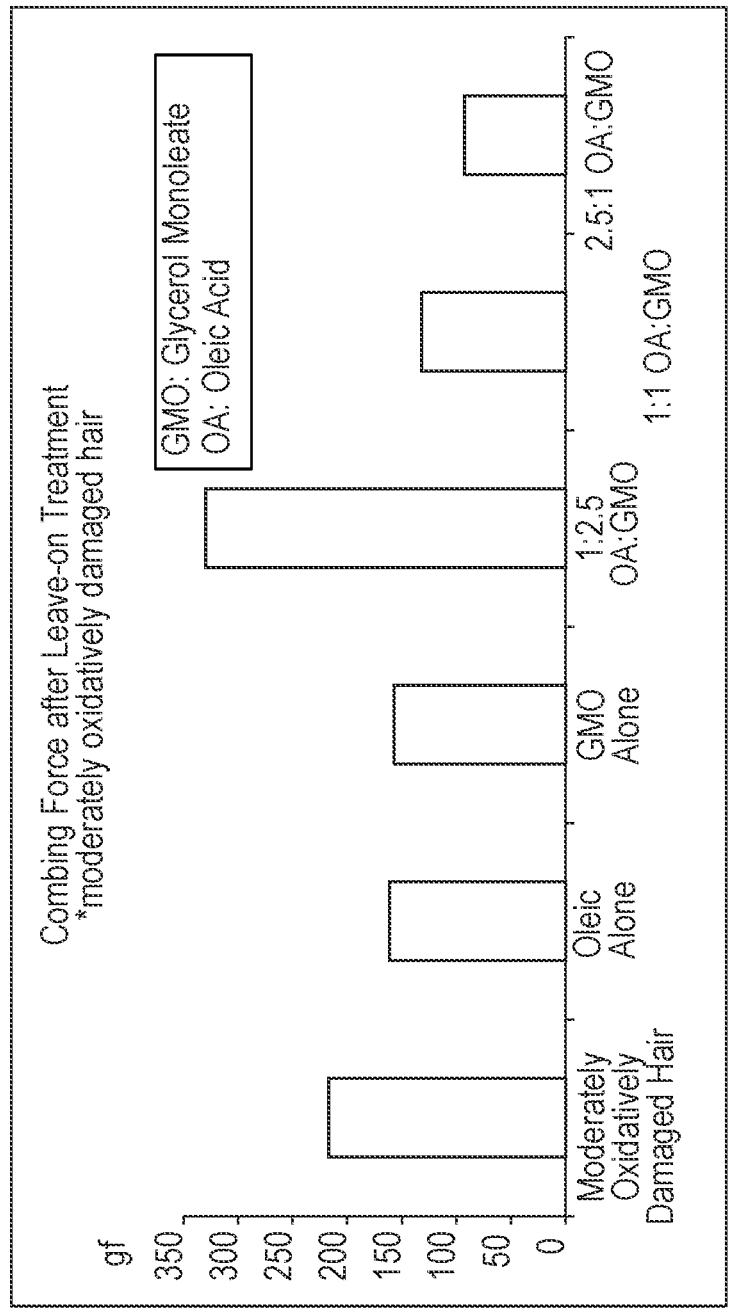
FIG. 1 is a graph of an optimum blend ratio of lipid and lipid enhancing agent demonstrating a measure force (gf) to comb moderately oxidatively-damaged hair.

All percentages and ratios used herein are by weight of the total composition, unless otherwise designated. All measurements are understood to be made at ambient conditions, where "ambient conditions" means conditions at about 25° C., under about one atmosphere of pressure, and at about 50% relative humidity (RH), unless otherwise designated. All numeric ranges are inclusive of narrower ranges; delineated upper and lower range limits are combinable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

"Apply" or "application" as used in reference to a composition, means to apply or spread the compositions of the present invention onto keratinous tissue such as the hair.

"Dermatologically acceptable" means that the compositions or components described are suitable for use in contact with human skin tissue without undue toxicity, incompatibility, instability, allergic response, and the like.

"Safe and effective amount" means an amount of a compound or composition sufficient to significantly induce a positive benefit "Leave-on," in reference to compositions, means compositions intended to be applied to and allowed to remain on the keratinous tissue. These leave-on compositions are to be distinguished from compositions which are applied to the hair and subsequently (in a few minutes or less) removed either by washing, rinsing, wiping, or the like. Leave-on compositions exclude rinse-off applications such as shampoos, rinse-off conditioners, facial cleansers, hand cleansers, body wash, or body cleansers.

"Log P" means octanol-water partition coefficient and is a physical property that describes a chemical's lipophilic and hydrophophilic characteristics. Log P is the logarithm of the ratio of a chemical's concentration in the octanol phase to its concentration in the aqueous phase of a two-phase system at equilibrium. The partition coefficient is a ratio of concentrations of un-ionized compound between the two solutions. Log P=Log 10 (partition coefficient). Partition coefficient=[organic]/[aqueous], where [organic] is the concentration of the compound of interest in the organic solvent (e.g., octanol), and [aqueous] is the concentration of the compound of interest in the water phase.

"Soluble" means at least about 0.1 g of solute dissolves in 100 ml of solvent, at 25° C. and 1 atm of pressure.

The term "substantially free from" or "substantially free of" as used herein means less than about 1%, or less than about 0.8%, or less than about 0.5%, or less than about 0.3%, or about 0%, by total weight of the composition.

"Hair," as used herein, means mammalian hair including scalp hair, facial hair and body hair, particularly on hair on the human head and scalp.

"Cosmetically acceptable," as used herein, means that the compositions, formulations or components described are suitable for use in contact with human keratinous tissue without undue toxicity, incompatibility, instability, allergic response, and the like. All compositions described herein which have the purpose of being directly applied to keratinous tissue are limited to those being cosmetically acceptable.

"Derivatives," as used herein, includes but is not limited to, amide, ether, ester, amino, carboxyl, acetyl, acid, salt and/or alcohol derivatives of a given compound.

"Polymer," as used herein, means a chemical formed from the polymerisation of two or more monomers. The term "polymer" as used herein shall include all materials made by the polymerisation of monomers as well as natural polymers. Polymers made from only one type of monomer are called homopolymers. Polymers made from two or more different types of monomers are called copolymers. The distribution of the different monomers can be calculated statistically or block-wise—both possibilities are suitable for the present invention. Except if stated otherwise, the term "polymer" used herein includes any type of polymer including homopolymers and copolymers.

"Volatile," as used herein, means those materials that are liquid under ambient conditions and which have a measurable vapor pressure at 25° C. Specifically the material have a boiling point at 1 atm of about 260° C. or less, preferably about 200° C. or less, more preferably about 150° C. or less and most preferably 100° C. or less.

"Lipid" as used herein, is a biological molecule which is insoluble in water while being soluble in fat and non-polar organic solvent. It typical contains either a long hydrocarbon chain or multiple linked aromatic rings. Long hydrocarbon chain can have six or more carbon atoms. "Lipid Enhancing Agent" is a material which further improves upon the hair fiber benefit provided by the lipid such as decreased combing.

Without being bound by theory, the improvement in fiber properties is achieved by the penetration of lipids from the hair care composition into the hair and incorporation into the lipid layers, such as the Cuticle Membrane Complex or the Cortex Membrane Complex. The lipid enhancing agent may contribute to more effective incorporation of these lipids into the lipid layer.

Lipids make up the cuticle membrane complex and cortex membrane complex (CMC) of the hair, which is the structural component that holds the hair proteins together. Therefore it stands that loss of lipids results in loss or weakening of the CMC and degradation of the hair structure. The hair care composition described herein recognizes that the impact of the loss of lipids leads to more moisture uptake in the hair at high humidity resulting in hair frizz. In addition, consumers can perceive that tip hair, which contains low levels of lipids (compared to root hair), is more damaged. It has been demonstrated that the level of hair lipids decreases upon age and insults, i.e. UV, color, washing and, in turn, this is also perceived as damage. It is likely that loss of lipids, which alters the arrangement of CMC, also impacts surface hair properties and hair shine.

It has been found that the combination of oleic acid and glyceryl monooleate in conditioner applications (in ratios of Oleic acid:GMO of about 1:1 to about 10:1, alternatively from about 1:1 to about 5:1, alternatively from about 2:1 to about 3:1) shows a synergistic effect compared to individual components at the same concentration, as seen in FIG. 1. In an embodiment the conditioner is a dry conditioner. It is perceived that GMO contributes to higher penetration of oleic acid into the hair fiber. It has also been found that other compounds, such as fatty acid monoesters of a polyol and saturated fatty alcohols can also be used as penetration enhancing materials. Thus, the hair care compositions described herein use unique blends of (a) unsaturated fatty acids (or unsaturated fatty alcohols) and (b) lipid enhancing agents. Lipid enhancing agents can enhance the benefit provided by the lipid material to the hair fiber and enabling improved softness and combability.

Lipid

The hair care composition described herein may contain one or more of an unsaturated fatty material wherein the molecule of said unsaturated fatty material comprises a linear or branched carbon chain with 8 to 22 carbon atoms, and one carbon-carbon double bond in a position of the said carbon chain between position C3 and position omega for the unsaturated fatty acid and between position C2 and position omega for the unsaturated fatty alcohol, and wherein the Log P of said unsaturated fatty material is less than 8, alternatively less than 7.5, alternatively less than 7.

The lipid may be present in a range from about 0.01% to 20%, alternatively in the range from about 0.05% to about 5%, alternatively in the range of from about 0.1% to about 2.5%, alternatively in the range of from about 0.1% to about 1.5%, by weight of the hair care composition.

Nonlimiting examples of an unsaturated fatty material include:
  i. an unsaturated fatty acid, non-limiting examples include myristoleic acid, palmitoleic acid, sapienic acid, oleic acid, elaidic acid, vaccenic acid, and nervonic acid. In an embodiment, the unsaturated fatty acid is oleic acid.
  ii. an unsaturated fatty alcohol, non-limiting examples include petroselenyl alcohol, erucyl alcohol, oleyl alcohol, palmitoleyl alcohol, vaccenyl alcohol, and Eicos-11-en-1-ol.

Lipid Enhancing Agent

The hair care composition described herein may contain one or more of a lipid enhancing agent.

The lipid enhancing agent may be present in the range of about 0.01% to about 10%, alternatively from about 0.01% to about 5%, alternatively from about 0.1% to about 2.5%, and alternatively from about 0.1% to about 0.5%, by weight of the hair care composition.

Nonlimiting examples of lipid enhancing agents include:
  i. a fatty acid monoester of a polyol wherein the molecule of the fatty acid component of such monoester contains a linear or branched carbon chain with 10 to 22 carbon atoms and wherein the fatty acid monoester of a polyol has a log P of less than 8, alternatively less than 7.5, alternatively less than 7, non-limiting examples include glyceryl monooleate, glycerol palmitoleate, 1-stearoyl-rac-glycerol, 2-oleoylglycerol, glycerol monoisostearate, ethylene glycol, monooleate. In an embodiment, the fatty acid monoester of the polyol is glyceryl monooleate.

ii. a saturated fatty alcohol wherein the molecule of the fatty alcohol contains a linear or branched carbon chain with 8 to 22 carbon atoms, non-limiting examples include 1-Octanol (capryl alcohol), pelargonic alcohol (1-nonanol), 1-Decanol (decyl alcohol, capric alcohol), Undecyl alcohol (1-undecanol, undecanol, Hendecanol), Lauryl alcohol (Dodecanol, 1-dodecanol), Tridecyl alcohol (1-tridecanol, tridecanol, isotridecanol), Myristyl alcohol (1-tetradecanol), Pentadecyl alcohol (1-pentadecanol, pentadecanol), cetyl alcohol (1-hexadecanol), Heptadecyl alcohol (1-n-heptadecanol, heptadecanol), stearyl alcohol (1-octadecanol), Nonadecyl alcohol (1-nonadecanol), arachidyl alcohol (1-eicosanol), Heneicosyl alcohol (1-heneicosanol), behenyl alcohol (1-docosanol).

iii. an ester of a saturated fatty alcohol wherein the molecule of said ester contains 10 to 44 total carbon atoms, non-limiting examples include 2-ethylhexanol, isostearyl isostearate, 2-hexyl-1-decanol.

In an embodiment, the unsaturated fatty acid is oleic acid and the fatty acid monoester of the polyol is glyceryl monooleate.

Compressed Propellant

The hair care composition described herein may comprise from about 25% to about 70%, alternatively from about 40% to about 60%, alternatively from about 50% to about 60%, by weight of the hair care composition.

The propellant may comprise one or more volatile materials, which in a gaseous state, may carry the other components of the concentrated hair care composition in particulate or droplet form. The propellant may have a boiling point within the range of from about −45° C. to about 5° C. The propellant may be liquefied when packaged in convention aerosol containers under pressure. The rapid boiling of the propellant upon leaving the aerosol foam dispenser may aid in the atomization of the other components of the hair care composition.

Aerosol propellants which may be employed in the hair care composition may include the chemically-inert hydrocarbons such as propane, n-butane, isobutane, cyclopropane, and mixtures thereof, as well as halogenated hydrocarbons such as dichlorodifluoromethane, 1,1-dichloro-1,1,2,2-tetrafluoroethane, 1-chloro-1,1-difluoro-2,2-trifluoroethane, 1-chloro-1,1-difluoroethylene, 1,1-difluoroethane, dimethyl ether, monochlorodifluoromethane, trans-1,3,3,3-tetrafluoropropene, and mixtures thereof. The propellant may comprise hydrocarbons such as isobutane, propane, and butane these materials may be used for their low ozone reactivity and may be used as individual components where their vapor pressures at 21.1° C. range from about 1.17 Bar to about 7.45 Bar, alternatively from about 1.17 Bar to about 4.83 Bar, and alternatively from about 2.14 Bar to about 3.79 Bar.

Non-Aqueous Volatile Solvent

The hair care compositions described herein may include a non-aqueous volatile solvent or a mixture of non-aqueous volatile solvents. In an embodiment, the hair care composition comprises a propellant and the hair care composition comprises from about 15% to about 75%, alternatively from about 25% to about 60%, alternatively from about 30% to about 50% of a non-aqueous volatile solvent, by weight of the hair care composition. In an embodiment, the hair care composition does not comprise a propellant and the hair care composition comprises from about 40% to about 99.8%, alternatively from about 50% to about 98%, alternatively from about 75% to about 90% of a non-aqueous volatile solvent, by weight of the hair care composition.

The non-aqueous volatile solvents useful herein may be relatively odorless and safe for use on human skin. Suitable volatile solvents may include $C_1$-$C_4$ alcohols and mixtures thereof. For example, ethanol may be used as the non-aqueous volatile solvent. Some other non-limiting examples of non-aqueous volatile solvents include methanol, propanol, isopropanol, butanol, and mixtures thereof.

Hydrophobically Modified Tapioca Starch

The hair care composition may comprise from about 0.1% to about 10% particulate tapioca starch, alternatively from about 0.1% to about 5% particulate tapioca starch, and alternatively from about 0.5% to about 3% particulate tapioca starch, by weight of the hair care composition.

The particulate tapioca starch may be selected from the group consisting of hydrophobically modified particulate tapioca starch, hydrophobically unmodified particulate tapioca starch, and combinations thereof. The ratio of hydrophobically modified particulate tapioca starch to unmodified particulate tapioca starch may be 2:1 or greater.

Hydrophobically modified particulate tapioca starches may be made by a variety of methods, including those discussed in U.S. Pat. Nos. 7,375,214, 7,799,909, 6,037,466, 2,852,404, 5,672,699, and 5,776,476.

Modified tapioca particulate starch may be an organically modified particulate tapioca starch or a silicone grafted particulate tapioca starch. Silicone grafted particulate tapioca starch may be purchased under the trade name Dry Flo TS and under the INCI name Tapioca Starch Polymethylsilsesquioxane. Silicone modified particulate tapioca starch may be produced by a reaction of methyl sodium siliconate (polymethylsilsesquioxane) and tapioca starch. Particulate tapioca starch may be sourced from the Cassava root by standard means know in the art. One example of a commercially available silicone modified particulate tapioca starch is CAS no. 68989-12-8.

Water

In an embodiment, the hair conditioning composition comprises from about 0.1% to about 10% water, alternatively less than 0.1% water, alternative about 0% water, by weight of the hair care composition.

pH of Compositions

In an embodiment, the pH of the hair care composition described herein is in the range of about 3 to about 9, and alternatively from about 4 to about 6.

Cationic Surfactant System

The hair care composition described herein can comprise a cationic surfactant system. The cationic surfactant system can be one cationic surfactant or a mixture of two or more cationic surfactants. Preferably, the cationic surfactant system is selected from: mono-long alkyl quaternized ammonium salt; a combination of mono-long alkyl quaternized ammonium salt and di-long alkyl quaternized ammonium salt; mono-long alkyl amidoamine salt; a combination of mono-long alkyl amidoamine salt and di-long alkyl quaternized ammonium salt, a combination of mono-long alkyl amindoamine salt and mono-long alkyl quaternized ammonium salt The cationic surfactant system can be included in the hair care composition at a level by weight of from about 0.1% to about 10%, alternatively from about 0.5% to about 8%, alternatively from about 0.8% to about 5%, and alternatively from about 1.0% to about 4%.

Mono-Long Alkyl Quaternized Ammonium Salt

The monoalkyl quaternized ammonium salt cationic surfactants that can be useful herein are those having one long alkyl chain which has from 12 to 30 carbon atoms, alternatively from 16 to 24 carbon atoms, and alternatively C18-22 alkyl group. The remaining groups attached to nitrogen can be independently selected from an alkyl group of from 1 to about 4 carbon atoms or an alkoxy, polyoxyalkylene, alkylamido, hydroxyalkyl, aryl or alkylaryl group having up to about 4 carbon atoms.

Mono-long alkyl quaternized ammonium salts useful herein can be those having the formula (I):

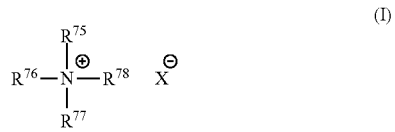

(I)

wherein one of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. Preferably, one of $R^{75}$, $R^{76}$, $R^{77}$ and $R^{78}$ is selected from an alkyl group of from 12 to 30 carbon atoms, more preferably from 16 to 24 carbon atoms, still more preferably from 18 to 22 carbon atoms, even more preferably 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof.

Non-limiting examples of such mono-long alkyl quaternized ammonium salt cationic surfactants include: behenyl trimethyl ammonium salt; stearyl trimethyl ammonium salt; cetyl trimethyl ammonium salt; and hydrogenated tallow alkyl trimethyl ammonium salt.

Mono-Long Alkyl Amidoamine Salt

Mono-long alkyl amines are also suitable as cationic surfactants. Primary, secondary, and tertiary fatty amines are useful. Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Useful amines in the present invention are disclosed in U.S. Pat. No. 4,275,055, Nachtigal, et al. These amines can also be used in combination with acids such as l-glutamic acid, lactic acid, hydrochloric acid, malic acid, succinic acid, acetic acid, fumaric acid, tartaric acid, citric acid, l-glutamic hydrochloride, maleic acid, and mixtures thereof; more preferably l-glutamic acid, lactic acid, citric acid. The amines herein are preferably partially neutralized with any of the acids at a molar ratio of the amine to the acid of from about 1:0.3 to about 1:2, more preferably from about 1:0.4 to about 1:1.

Di-Long Alkyl Quaternized Ammonium Salt

Di-long alkyl quaternized ammonium salt is preferably combined with a mono-long alkyl quaternized ammonium salt or mono-long alkyl amidoamine salt. It is believed that such combination can provide easy-to-rinse feel, compared to single use of a monoalkyl quaternized ammonium salt or mono-long alkyl amidoamine salt. In such combination with a mono-long alkyl quaternized ammonium salt or mono-long alkyl amidoamine salt, the di-long alkyl quaternized ammonium salts are used at a level such that the wt % of the dialkyl quaternized ammonium salt in the cationic surfactant system is in the range of preferably from about 10% to about 50%, more preferably from about 30% to about 45%.

The dialkyl quaternized ammonium salt cationic surfactants useful herein are those having two long alkyl chains having 12-30 carbon atoms, preferably 16-24 carbon atoms, more preferably 18-22 carbon atoms. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Di-long alkyl quaternized ammonium salts useful herein are those having the formula (II):

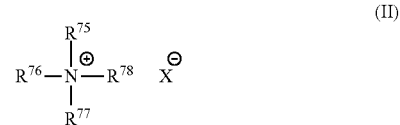

(II)

wherein two of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. Preferably, one of $R^{75}$, $R^{76}$, $R^{77}$ and $R^{78}$ is selected from an alkyl group of from 12 to 30 carbon atoms, more preferably from 16 to 24 carbon atoms, still more preferably from 18 to 22 carbon atoms, even more preferably 22 carbon atoms; the remainder of $R^{75}$, $R^{76}$, $R^{77}$ and $R^{78}$ are independently selected from $CH_3$, $C_2H_5$, $C_2H_4OH$, and mixtures thereof; and X is selected from the group consisting of Cl, Br, $CH_3OSO_3$, $C_2H_5OSO_3$, and mixtures thereof. Such dialkyl quaternized ammonium salt cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride. Such dialkyl quaternized ammonium salt cationic surfactants also include, for example, asymmetric dialkyl quaternized ammonium salt cationic surfactants.

Additional Components
Silicone Conditioning Agent

The compositions of the present invention may contain one or more silicone conditioning agents. Examples of the silicones include dimethicones, dimethiconols, cyclic silicones, methylphenyl polysiloxane, and modified silicones with various functional groups such as amino groups, quaternary ammonium salt groups, aliphatic groups, alcohol groups, carboxylic acid groups, ether groups, epoxy groups, sugar or polysaccharide groups, fluorine-modified alkyl groups, alkoxy groups, or combinations of such groups. Such silicones may be soluble or insoluble in the aqueous (or non-aqueous) product carrier. In the case of insoluble liquid silicones, the polymer can be in an emulsified form with droplet size of about 10 nm to about 30 micrometers.

In an embodiment, the hair care composition may comprise from about 0.01% to about 50% silicone, alternatively from about 0.5% to about 30% silicone, alternatively from about 1% to about 25% silicone, by weight of the hair care composition.

Nonionic Polymers

The hair care compositions described herein may also further comprise a nonionic polymer. According to an embodiment, the conditioning agent for use in the hair care composition of the present invention may include a polyalkylene glycol polymer. For example, polyalkylene glycols having a molecular weight of more than about 1000 are useful herein. Useful are those having the following general formula (VIII):

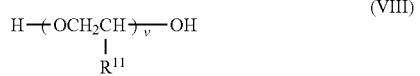

(VIII)

wherein $R^{11}$ is selected from the group consisting of H, methyl, and mixtures thereof; and v is the number of ethoxy units. The polyalkylene glycols, such as polyethylene glycols, can be included in the hair care compositions of the present invention at a level of from about 0.001 wt. % to about 10 wt. %. In an embodiment, the polyethylene glycol is present in an amount up to about 5 wt. % based on the weight of the composition. Polyethylene glycol polymers useful herein are PEG-2M (also known as Polyox WSR® N-10, which is available from Union Carbide and as PEG-2,000); PEG-5M (also known as Polyox WSR® N-35 and Polyox WSR® N-80, available from Union Carbide and as PEG-5,000 and Polyethylene Glycol 300,000); PEG-7M (also known as Polyox WSR® N-750 available from Union Carbide); PEG-9M (also known as Polyox WSR® N-3333 available from Union Carbide); and PEG-14 M (also known as Polyox WSR® N-3000 available from Union Carbide).

Organic Conditioning Materials

The hair care compositions described herein may also comprise at least one organic conditioning material such as oil or wax, either alone or in combination with other conditioning agents, such as the silicones described above. The organic material can be non-polymeric, oligomeric or polymeric. It may be in the form of oil or wax and may be added in the formulation neat or in a pre-emulsified form. Some non-limiting examples of organic conditioning materials include, but are not limited to: i) hydrocarbon oils; ii) polyolefins, iii) fatty esters, iv) fluorinated conditioning compounds, v) alkyl glucosides and alkyl glucoside derivatives; vi) quaternary ammonium compounds; and mixtures thereof.

Rheology Modifier/Suspending Agents

In an embodiment, the hair care compositions described herein may comprise a rheology modifier. The rheology modifier increases the substantivity and stability of the composition, improve feel and consumer's use experience (e.g. non-dripping, spreadability, etc). Any suitable rheology modifier can be used. In an embodiment, the hair care composition may comprise from about 0.05% to about 10% of a rheology modifier, in a further embodiment, from about 0.1% to about 10% of a rheology modifier, in yet a further embodiment, from about 0.5% to about 2% of a rheology modifier, in a further embodiment, from about 0.7% to about 2% of a rheology modifier, and in a further embodiment from about 1% to about 1.5% of a rheology modifier. In an embodiment, the rheology modifier may be a polyacrylamide thickener. In an embodiment, the rheology modifier may be a polymeric rheology modifier.

In an embodiment, the hair care compositions described herein may comprise rheology modifiers that are homopolymers based on acrylic acid, methacrylic acid or other related derivatives, non-limiting examples include polyacrylate, polymethacrylate, polyethylacrylate, and polyacrylamide.

In another embodiment, the rheology modifiers may be alkali swellable and hydrophobically-modified alkali swellable acrylic copolymers or methacrylate copolymers non-limiting examples include acrylic acid/acrylonitrogen copolymer, acrylates/steareth-20 itaconate copolymer, acrylates/ceteth-20 itaconate copolymer, acrylates/aminoacrylates copolymer, acrylates/steareth-20 methacrylate copolymer, acrylates/beheneth-25 methacrylate copolymer, acrylates/steareth-20 methacrylate crosspolymer, acrylates/vinylneodecanoate crosspolymer, and acrylates/C10-C30 alkyl acrylate crosspolymer.

In a further embodiment, the rheology modifiers may be crosslinked acrylic polymers, a non-limiting example includes carbomers.

In a further embodiment, the rheology modifiers may be alginic acid-based materials; non-limiting examples include sodium alginate, and alginic acid propylene glycol esters.

In a further embodiment, the rheology modifier may be an associative polymeric thickeners, non-limiting examples include: Hydrophobically modified cellulose derivatives; Hydrophobically modified alkoxylated urethane polymers, nonlimiting example include PEG-150/decyl alcohol/SMDI copolymer, PEG-150/stearyl alcohol/SMDI copolymer, polyurethane-39; Hydrophobically modified, alkali swellable emulsions, non-limiting examples include hydrophobically modified polyacrylates, hydrophobically modified polyacrylic acids, and hydrophobically modified polyacrylamides; hydrophobically modified polyethers wherein these materials may have a hydrophobe that can be selected from cetyl, stearyl, oleayl, and combinations thereof, and a hydrophilic portion of repeating ethylene oxide groups with repeat units from 10-300, in another embodiment from 30-200, in a further embodiment from 40-150. Non-limiting examples of this class include PEG-120-methylglucose dioleate, PEG-(40 or 60) sorbitan tetraoleate, PEG-150 pentaerythrityl tetrastearate, PEG-55 propylene glycol oleate, PEG-150 distearate.

In a further embodiment, the rheology modifier may be cellulose and derivatives; nonlimiting examples include microcrystalline cellulose, carboxymethylcelluloses, hydroxyethylcellulose, hydroxypropylcellulose, hydroxypropylmethylcellulose, methylcellulose, ethylcellulose, nitro cellulose, cellulose sulfate, cellulose powder, and hydrophobically modified celluloses.

In an embodiment, the rheology modifier may be a guar and guar derivatives; nonlimiting examples include hydroxypropyl guar, and hydroxypropyl guar hydroxypropyl trimonium chloride.

In an embodiment, the rheology modifier may be polyethylene oxide, polypropylene oxide, and POE-PPO copolymers.

In an embodiment, the rheology modifier may be polyvinylpyrrolidone, crosslinked polyvinylpyrrolidone and derivatives. In a further embodiment, the rheology modifier may be polyvinylalcohol and derivatives.

In a further embodiment, the rheology modifier may be polyethyleneimine and derivatives.

In another embodiment, the rheology modifier may be silicas; nonlimiting examples include fumed silica, precipitated silica, and silicone-surface treated silica.

In an embodiment, the rheology modifier may be water-swellable clays non-limiting examples include laponite, bentolite, montmorilonite, smectite, and hectonite.

In an embodiment, the rheology modifier may be gums nonlimiting examples include xanthan gum, guar gum, hydroxypropyl guar gum, Arabia gum, tragacanth, galactan, carob gum, karaya gum, and locust bean gum.

In a further embodiment, the rheology modifier may be, dibenzylidene sorbitol, karaggenan, pectin, agar, quince seed (*Cydonia oblonga* Mill), starch (from rice, corn, potato, wheat, etc), starch-derivatives (e.g. carboxymethyl starch, methylhydroxypropyl starch), algae extracts, dextran, succinoglucan, and pulleran.

Non-limiting examples of rheology modifiers include acrylamide/ammonium acrylate copolymer (and)polyisobutene (and) polysorbate 20, acrylamide/sodium acryloyldimethyl taurate copolymer/isohexadecane/polysorbate 80, acrylates copolymer; acrylates/beheneth-25 methacrylate copolymer, acrylates/C10-C30 alkyl acrylate crosspolymer, acrylates/steareth-20 itaconate copolymer, ammonium polyacrylate/Isohexadecane/PEG-40 castor oil, C12-16 alkyl PEG-2 hydroxypropylhydroxyethyl ethylcellulose (HM-EHEC), carbomer, crosslinked polyvinylpyrrolidone (PVP), dibenzylidene sorbitol, hydroxyethyl ethylcellulose (EHEC), hydroxypropyl methylcellulose (HPMC), hydroxypropyl methylcellulose (HPMC), hydroxypropylcellulose (HPC), methylcellulose (MC), methylhydroxyethyl cellulose (MEHEC), PEG-150/decyl alcohol/SMDI copolymer, PEG-150/stearyl alcohol/SMDI copolymer, polyacrylamide/C13-14 isoparaffin/laureth-7; polyacrylate 13/polyisobutene/polysorbate 20; polyacrylate crosspolymer-6, polyamide-3; polyquaternium-37 (and) hydrogenated polydecene (and) trideceth-6, polyurethane-39, sodium acrylate/acryloyldimethyltaurate/dimethylacrylamide, crosspolymer (and) isohexadecane (and) polysorbate 60; sodium polyacrylate. Exemplary commercially-available rheology modifiers include ACULYN™ 28, Klucel™ M CS, Klucel™ H CS, Klucel™ G CS, SYLVACLEAR™ AF1900V, SYLVACLEAR™ PA1200V, Benecel™ E10M, Benecel™ K35M, Optasense™ RMC70, ACULYN™33, ACULYN™46, ACULYN™22, ACULYN™44, Carbopol Ultrez™ 20, Carbopol Ultrez™ 21, Carbopol Ultrez™ 10, Carbopol Ulterez™ 30, Carbopol™ 1342, Carbopol™ 934, Carbopol™ 940, Carbopol™ 950, Carbopol™ 980, and Carbopol™ 981, Acrysol™ 22, Sepigel™ 305, Simulgel™600, Sepimax Zen, and combinations thereof.

The hair care compositions described herein may comprise one or more non-polar solvents. Non-limiting examples of non-polar solvents are isoparaffin, mineral oil, silicone oil, natural oils such as olive oil, argan oil, jojoba oil, passion fruit oil.

Other Optional Ingredients

The hair care compositions described herein may also comprise any other suitable optional ingredients as desired. For example, the hair care compositions may comprise other active or inactive ingredients.

In an embodiment, a scalp health active may be added to provide scalp benefits. This group of materials is varied and provides a wide range of benefits including anti-dandruff, anti-fungal, anti-microbial, moisturization, barrier improvement, and anti-oxidant, anti-itch, and sensates. Such health actives include but are not limited to: zinc pyrithione, climbazole, octopirox, vitamin E and F, salicylic acid, glycols, glycolic acid, PCA, PEGs, erythritol, glycerin, lactates, hyaluronates, allantoin and other ureas, betaines, sorbitol, glutamates, xylitols, menthol, menthyl lactate, isocyclomone, benzyl alcohol, and natural extracts/oils including peppermint, spearmint, argan, jojoba and aloe. The compositions may include other common hair ingredients. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of nonlimiting materials that can be added to the composition herein. Examples of these ingredient classes include, but are not limited to: aesthetic components such as fragrances, pigments, colorings/colorants, essential oils, sensates, etcantifoaming agents, antimicrobial agents, biological additives, buffering agents, bulking agents, chelating agents, chemical additives, astringents, biocides, film formers or materials, pH adjusters, reducing agents, sequestrants, and surfactants.

EXAMPLES & DATA

The following examples and data illustrate the hair care compositions described herein. The exemplified hair care compositions may be prepared by conventional formulation and mixing techniques. It will be appreciated that other modifications of the formulations and dosages of foam described herein within the skill of those in the shampoo formulation art can be undertaken without departing from the spirit and scope of the formulations and dosages of foam described herein. All parts, percentages, and ratios herein are by weight unless otherwise specified. Some components may come from suppliers as dilute solutions. The amount stated reflects the weight percent of the active material, unless otherwise specified.

Method for Combing Force for Dry Hair:

A moderately oxidatively-damaged hair switch or physically damaged virgin hair switch (with weight of 4 gram and length of 8 inches) is placed in an apparatus containing two combs separated by a vertical distance of 6 inches. This double combing apparatus is attached to an Instron Model 5564. The switch is combed 5 times with a fine-tooth comb and hanged onto the Instron load cell. Then, the hair switch is placed in the double comb apparatus. The Instron pulls the hair vertically at a rate of 10 mm/min until the hair switch clears the final comb. The peak force as the switch passes through the top comb is reported.

FIG. 1 is a measure of force (in gram force—gf) required to comb moderately oxidatively-damaged hair that is treated with an aqueous/ethanol rinse-off formulation containing 2.5% total conditioning agent (lipid+lipid enhancing agent):
- A: 0.71% Oleic acid and 1.79% GMO (Oleic acid: GMO=1:2.5)
- B: 1.25% Oleic acid and 1.25% GMO (Oleic acid: GMO=1:1)
- C: 1.79% Oleic acid and 0.71% GMO (Oleic acid: GMO=2.5:1)

These measurements are compared with the corresponding measurements from untreated moderately oxidatively damaged hair and hair treated with leave on treatment containing 2.5% oleic acid. These measurements are also compared with moderately oxidatively-damaged hair treated with leave on treatment containing 2.5% glyceryl monoleate. It can be seen that hair treated with treatments containing lipid plus lipid enhancing agent at a ratio of 1:1 and 2.5:1 show better combing versus untreated moderately oxidatively-damaged hair and treatments containing only lipid (oleic acid) or only lipid enhancing agent (glyceryl monooleate). Thus, the combination of oleic acid and glyceryl monooleate shows a synergistic effect on combability.

TABLE 1

| Treatments | Combing Force (gf) |
| --- | --- |
| Untreated Moderately Oxidatively Damaged Hair | 217 |
| Oleic Alone | 161 |
| Glyceryl monooleate | 157 |
| 1:2.5 Oleic Acid:Glyceryl monooleate | 330 |
| 1:1 Oleic acid:Glyceryl monooleate | 132 |
| 2.5:1 Oleic acid:Glyceryl monooleate | 93 |

Figure 2:
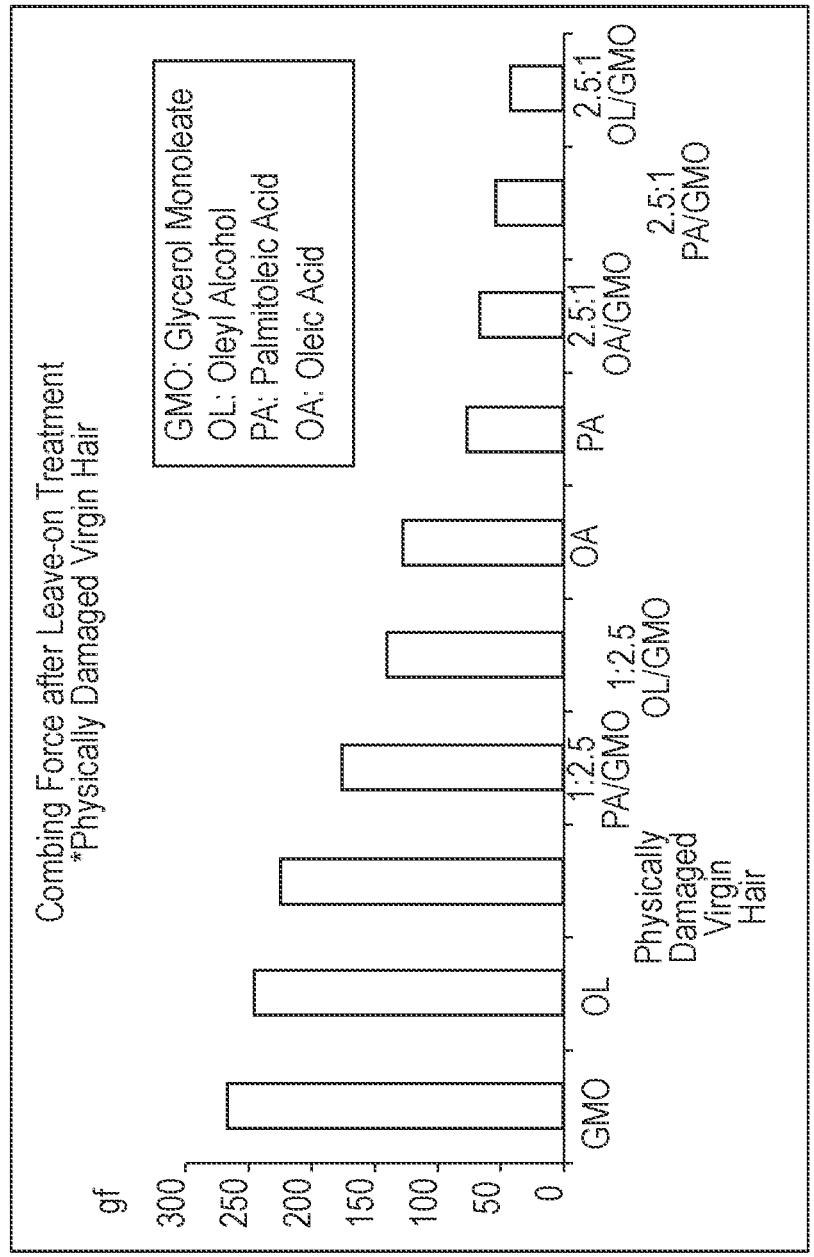
FIG. 2 is a graph of an optimum blend ratio of lipid and lipid enhancing agent demonstrating a measure force (gf) to comb physically damaged virgin hair.

FIG. 2 shows the combing forced (measured in gram force—gf) for physically damaged virgin hair which is treated with an aqueous/ethanol leave-on formulations containing 2.5% total conditioning agent (lipid+lipid enhancing agent):
 1.79% Oleic acid and 0.71% GMO (Oleic acid: GMO=2.5:1)
 0.71% Palmitoleic acid and 1.79% GMO (Palmitoleic acid:GMO=1:2.5)
 1.97% Palmitoleic acid and 0.71% GMO (Palmitoleic acid:GMO=2.5:1)
 0.71% Oleyl alcohol and 1.79% GMO (Palmitoleic acid: GMO=1:2.5)
 1.97% Oleyl alcohol and 0.71% GMO (Palmitoleic acid: GMO=2.5:1)

These measurements are compared with the corresponding measurements from untreated physically damaged virgin hair and hair treated with leave on treatment containing 2.5% oleic acid. These measurements are also compared with physically damaged virgin hair treated with leave on treatment containing 2.5% glyceryl monoleate.

It can be seen that hair treated with treatments containing lipid plus lipid enhancing agent at a ratio of 2.5:1 show better combing versus untreated physically damaged virgin hair and treatments containing only lipid (palmitoleic acid, oleic acid or oleyl alcohol) or only lipid enhancing agent (glyceryl monooleate).

TABLE 2

| Treatments | Combing Force (gf) |
| --- | --- |
| GMO | 268 |
| OL | 246 |
| Physically Damaged Virgin Hair | 225 |
| 1:2.5 PA/GMO | 176 |
| 1:2.5 OL/GMO | 142 |
| OA | 128 |
| PA | 76 |
| 2.5:1 OA/GMO | 66 |
| 2.5:1 PA/GMO | 53 |
| 2.5:1 OL/GMO | 42 |

Table 3 below summarizes and corresponds to moderately oxidatively-damaged hair treated with leave-on treatment. Materials 1-5 performed well in terms of hair combability, whereas materials 6-11 shows poor performance. The data shows that optimum efficacy is achieved by materials that have the following characteristics:
 a. Log P<8 alternatively less than 7.5, and alternatively less than 7; higher Log P corresponds to increased hydrophobicity (1-7, 10, 11 vs. 8,9);
 b. Material carbon chain length between C10 and C22 (1-5 vs. 8);
 c. Monounsaturation of the carbon chain (4 vs. 7 and 11).

TABLE 3

| | Material | LogP | Double Bonds in Chain | Olefin Position | Size of C Chain | Total Carbons | MW | Structure |
| --- | --- | --- | --- | --- | --- | --- | --- | --- |
| 1 | Glyceryl alpha-monooleate | 6.3 | 1 | Δ9 | 18 | 21 | 357 | Polyol monoester |
| 2 | Ethyleneglycol monooleate | 6.9 | 1 | Δ9 | 18 | 20 | 326 | Polyol monoester |
| 3 | Oleyl Alcohol | 7 | 1 | Δ9 | 18 | 18 | 268 | Fatty alcohol |
| 4 | Oleic acid | 7 | 1 | Δ9 | 18 | 18 | 282 | Fatty acid |
| 5 | Palmitoleic Acid | 6.6 | 1 | Δ9 | 16 | 16 | 254 | Fatty acid |
| 6 | Methyl Oleate | 8 | 1 | Δ9 olefin | 18 | 19 | 296 | Simple Ester |
| 7 | Stearic Acid | 8 | 0 | | 18 | 18 | 284 | Fatty acid |
| 8 | Glyceryl trioleate | 9 | 1 | Δ9 olefin | 18 | 57 | 885 | Triglyceride ester |
| 9 | Erucic acid | 9 | 1 | Δ13 olefin | 22 | 22 | 339 | Fatty acid |
| 10 | Propyleneglycol monooleate | 7.5 | 1 | Δ9 olefin | 18 | 18 | 340 | Polyol monoester |

TABLE 3-continued

| | Material | LogP | Double Bonds in Chain | Olefin Position | Size of C Chain | Total Carbons | MW | Structure |
|---|---|---|---|---|---|---|---|---|
| 11 | Linoleic Acid | 6.4 | 2 | Δ9, Δ12 olefin | 18 | 18 | 280 | Fatty acid |

Figure 3:
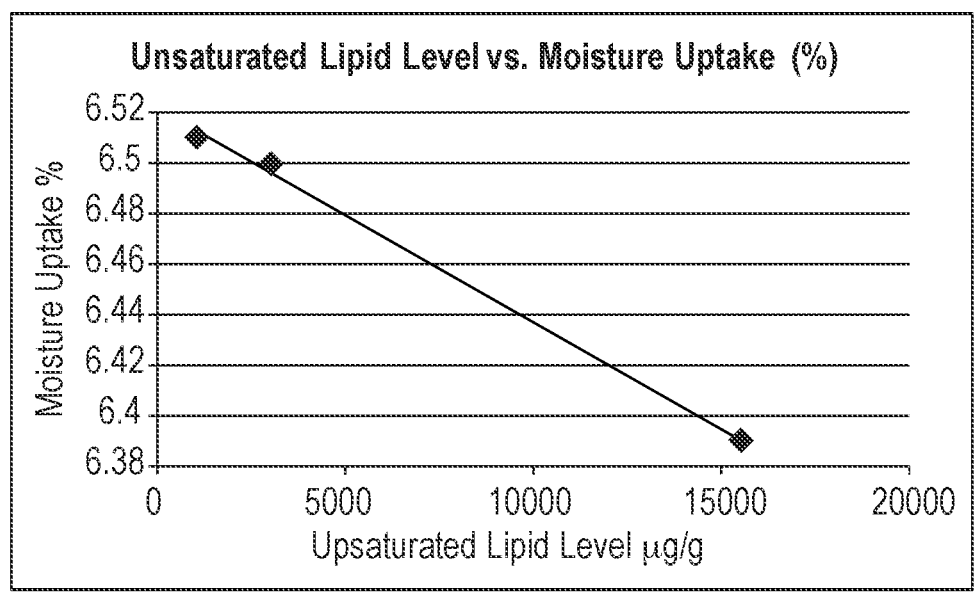
FIG. 3 is a graph of unsaturated lipid level versus amount of moisture uptake in hair.

Another indication of beneficial effect of the lipid in the hair interior can be demonstrated by decreased moisture absorption in the hair. This is measured technically by Dynamic Vapor Sorption (DVS) method. Our data demonstrate that there is a good correlation between unsaturated lipid content and DVS (see FIG. 3 and Table 4 below). More specifically, the higher the unsaturated lipid content, the lower the water absorption measured.

TABLE 4

Unsaturated Lipid Level versus Moisture Uptake

| Moisture Uptake (%) | Unsaturated Lipid Level μg/g |
|---|---|
| 6.51 | 1027 |
| 6.5 | 2978 |
| 6.39 | 15490 |

DVS Measurement:

An amount of 25-30 mg of hair with length of approximately 1 cm is weighed and hold for equilibration at 0% RH for 16 hours. After the 16-hour period, the RH is increased to 10% and maintained at this level for 6 hours. Then, the RH is increased by 10% after every 6 hours interval until it reaches 90% RH. The % water reduction is calculated as follows:

A=Amount of water absorbed by the hair treated with composition containing the lipid and/or lipid enhancing material.

B=Amount of water absorbed by the hair treated with control composition (only carrier) containing no lipid and/or lipid enhancing material % Water reduction=$[(B-A) \times 100]/B$ Leave-on Hair Treatment Using Neat Material An amount of 0.4 ml of neat oleic acid is thoroughly spread on a moderately oxidatively-damaged hair switch (with weight 4 g and length of 8 inches). The treatment is repeated to two additional switches. The treated hair switches are allowed to rest for 24 hours under controlled temperature and relative humidity conditions (27° C. and 50% RH). After this time period, each hair switch is washed with a clarifying shampoo (see shampoo washing protocol below) and allowed to air dry for 24 hours under controlled temperature and relative humidity conditions (27° C. and 50% RH). The combing force is measured for each switch and an average for the three switches is calculated. The shampoo washing and drying is repeated for 4 more cycles and the combing force measurement is repeated. The above experiment is repeated replacing the neat oleic acid with neat:

a. Linoleic acid
b. Olive oil (a triglyceride ester oil)

Combing Force Results for Hair Treated with Neat Materials (Described Above)

Hair treated with monounsaturated fatty acid, such as oleic acid, show better combability (lower combing force) than hair treated with fatty acids containing multiple carbon-carbon double bonds, such as linoleic acid (see example 1 versus example 2). In addition, triglycerides of fatty acids (olive oil) provide good combability, but the benefit is not durable over five washes (see example 3 versus examples 1 and 2).

TABLE 5

| Ex. | Treatment | 1 Wash (gf) | 5 Washes (gf) |
|---|---|---|---|
| 1 | Oleic Acid | 24 | 58 |
| 2 | Linoleic Acid | 27 | 96 |
| 3 | Olive Oil (triglyceride) | 57 | 133 |

EtOH/H$_2$O Leave-on Treatments

Single material mixtures: 500 mg of a lipid or a lipid enhancing agent is weighed into a 20 mL vial. 19.5 g of 50/50(v/v) ethanol water mixture is then added to the vial and capped. The mixture is then agitated for 30 seconds.

Shampoo Washing Protocol:

An amount of 0.10 g of clarifying shampoo per gram of hair is spread via a syringe onto separate hair switch. Each application consists of adding shampoo to the hair, milking for 30 seconds followed by rinsing for 30 seconds. Shampoo is then reapplied (0.1 g/g), milked for 30 seconds and rinsed for 30 seconds.

Leave-on Treatments with Aqueous/Ethanolic Lipid Compositions a. Method of Making of Aqueous/Ethanolic Leave-on Treatment Compositions The ingredients of each composition in Table 3 are placed in a 200-mL vial and a stopper is placed on the vial. The vial is then agitated or mixed for 30 seconds to a uniform composition.

b. Hair Treatment with Aqueous/Ethanolic Leave-on Treatment Compositions

An amount 0.8 mL of the aqueous/ethanolic compositions of Table 3 are applied onto a moderately oxidatively-damaged hair switch (with weight 4 g and length of 8 inches) and then massaged onto the hair for 60 seconds. The same treatment is repeated to two additional switches. The treated hair switches are allowed to rest for 24 hours under controlled temperature and relative humidity conditions (27° C. and 50% RH). After this time period, each hair switch is washed with a clarifying shampoo (see shampoo washing protocol above) and allowed to air dry for 24 hours under controlled temperature and relative humidity conditions (27° C. and 50% RH). The combing force is measured for each switch and an average for the three switches is calculated. The shampoo washing and drying is repeated for 4 more cycles and the combing force measurement is repeated.

Aqueous/Ethanolic Leave on Treatment Results

As Table 6 indicates, hair treated with aqueous/ethanolic leave on treatments containing materials with monounsaturated carbon chains in their molecule and exhibit Log P less than 8 (such as oleic acid, palmitoleic acid, and oleyl alcohol) show better combability than hair treated with aqueous/ethanolic leave on treatments containing materials with monounsaturated carbon chains in their molecule and exhibit Log P higher than 8 (see examples 1-5 versus examples 8). However, hair treated with aqueous/ethanolic leave-on treatments with α,β-unsaturated fatty acids, show inferior combability than hair treated with aqueous/ethanolic leave on treatments containing materials with monounsaturated carbon chains in their molecule, wherein the carbon-carbon double bond is not in the α,β-position in relation to the carbonyl functional group (see examples 6 and 7 versus examples 1-5. In addition there is a synergistic combing benefit when hair is treated with an aqueous/ethanolic leave on treatment containing when oleic acid and glyceryl monooleate in a ratio of 1:1 or 2.5:1 oleic acid to glyceryl monooleate. This treatment shows better combing than treatments that contain only glyceryl monoleate or oleic acid (see example 9 and 10 versus examples 1 and 4). A similar synergistic benefit is observed when hair is treated with other aqueous leave on treatments containing palmitoleic acid or oleyl alcohol in combination with glyceryl monoleate (see examples 12 versus example 2 and 1; and example 14 versus examples 2 and 5).

TABLE 6

| Ingredient | Ex 1 | Ex 2 | Ex 3 | Ex 4 | Ex 5 | Ex 6 | Ex 7 | Ex 8 | Ex 9 | Ex 10 | Ex 11 |
|---|---|---|---|---|---|---|---|---|---|---|---|
| Water | 48.75 | 48.75 | 48.75 | 48.75 | 48.75 | 48.75 | 48.75 | 48.75 | 48.75 | 48.75 | 48.75 |
| Ethanol | 48.75 | 48.75 | 48.75 | 48.75 | 48.75 | 48.75 | 48.75 | 48.75 | 48.75 | 48.75 | 48.75 |
| Glycerol alpha-monooleate[1] | 2.50 | 0.00 | 0.00 | 0.00 | 0.00 | 0.00 | 0.00 | 0.00 | 0.71 | 1.25 | 1.79 |
| Palmitoleic Acid[2] | 0.00 | 2.50 | 0.00 | 0.00 | 0.00 | 0.00 | 0.00 | 0.00 | 0.00 | 0.00 | 0.00 |
| Ethylene glycol-monooleate[2] | 0.00 | 0.00 | 2.50 | 0.00 | 0.00 | 0.00 | 0.00 | 0.00 | 0.00 | 0.00 | 0.00 |
| Oleic acid[3] | 0.00 | 0.00 | 0.00 | 2.50 | 0.00 | 0.00 | 0.00 | 0.00 | 1.79 | 1.25 | 0.71 |
| Oleyl Alcohol[2] | 0.00 | 0.00 | 0.00 | 0.00 | 2.50 | 0.00 | 0.00 | 0.00 | 0.00 | 0.00 | 0.00 |
| 2-Heptenoic acid[2] | 0.00 | 0.00 | 0.00 | 0.00 | 0.00 | 2.50 | 0.00 | 0.00 | 0.00 | 0.00 | 0.00 |
| 2-Hexadecenoic acid[2] | 0.00 | 0.00 | 0.00 | 0.00 | 0.00 | 0.00 | 0.00 | 0.00 | 0.00 | 0.00 | 0.00 |
| Methyl Oleate[2] | 0.00 | 0.00 | 0.00 | 0.00 | 0.00 | 0.00 | 0.00 | 0.00 | 0.00 | 0.00 | 0.00 |
| DiisopropylAdipate | 0.00 | 0.00 | 0.00 | 0.00 | 0.00 | 0.00 | 0.00 | 0.00 | 0.00 | 0.00 | 0.00 |
| Isodecane | 0.00 | 0.00 | 0.00 | 0.00 | 0.00 | 0.00 | 0.00 | 0.00 | 0.00 | 0.00 | 0.00 |
| Histidine[4] | 0.00 | 0.00 | 0.00 | 0.00 | 0.00 | 0.00 | 0.00 | 0.00 | 0.00 | 0.00 | 0.00 |
| Niacinamide[5] | 0.00 | 0.00 | 0.00 | 0.00 | 0.00 | 0.00 | 0.00 | 0.00 | 0.00 | 0.00 | 0.00 |
| Caffeine[6] | 0.00 | 0.00 | 0.00 | 0.00 | 0.00 | 0.00 | 0.00 | 0.00 | 0.00 | 0.00 | 0.00 |
| Panthenol[7] | 0.00 | 0.00 | 0.00 | 0.00 | 0.00 | 0.00 | 0.00 | 0.00 | 0.00 | 0.00 | 0.00 |
| Benzyl Alcohol[8] | 0.00 | 0.00 | 0.00 | 0.00 | 0.00 | 0.00 | 0.00 | 0.00 | 0.00 | 0.00 | 0.00 |
| Isostearyl Isostearate[9] | 0.00 | 0.00 | 0.00 | 0.00 | 0.00 | 0.00 | 0.00 | 0.00 | 0.00 | 0.00 | 0.00 |
| Combing Force(gf)1 | 104 | 124 | 140 | 161 | 201 | 255 | 273 | 316 | 93 | 132 | 330 |
| Combing Force(gf)2 | | | | | | | | | | | |

| | Ex 12 | Ex 13 | Ex 14 | Ex 15 | Ex 16 | Ex 17 | Ex 18 | Ex 19 | Ex 20 | Ex 21 | Ex 22 |
|---|---|---|---|---|---|---|---|---|---|---|---|
| Water | 48.75 | 48.75 | 48.75 | 48.75 | 48.75 | 48.75 | 48.75 | 48.75 | 48.75 | 47.21 | 47.21 |
| Ethanol | 48.75 | 48.75 | 48.75 | 48.75 | 48.75 | 48.75 | 48.75 | 48.75 | 48.75 | 48.75 | 48.75 |
| Glycerol alpha-monooleate | 0.71 | 1.79 | 0.71 | 1.79 | 0.71 | 2.50 | 0.00 | 0.00 | 0.00 | 0.71 | 1.25 |
| Palmitoleic Acid | 1.79 | 0.71 | 0.00 | 0.00 | 0.00 | 0.00 | 2.50 | 0.00 | 0.00 | 0.00 | 0.00 |
| Ethylene glycol-monooleate | 0.00 | 0.00 | 0.00 | 0.00 | 0.00 | 0.00 | 0.00 | 0.00 | 0.00 | 0.00 | 0.00 |
| Oleic acid | 0.00 | 0.00 | 0.00 | 0.00 | 1.79 | 0.00 | 0.00 | 2.50 | 0.00 | 1.79 | 1.25 |
| Oleyl Alcohol | 0.00 | 0.00 | 1.79 | 0.71 | 0.00 | 0.00 | 0.00 | 0.00 | 2.50 | 0.00 | 0.00 |
| 2-Heptenoic acid | 0.00 | 0.00 | 0.00 | 0.00 | 0.00 | 0.00 | 0.00 | 0.00 | 0.00 | 0.00 | 0.00 |
| 2-Hexadecenoic acid | 0.00 | 0.00 | 0.00 | 0.00 | 0.00 | 0.00 | 0.00 | 0.00 | 0.00 | 0.00 | 0.00 |
| Methyl Oleate | 0.00 | 0.00 | 0.00 | 0.00 | 0.00 | 0.00 | 0.00 | 0.00 | 0.00 | 0.00 | 0.00 |
| DiisopropylAdipate | 0.00 | 0.00 | 0.00 | 0.00 | 0.00 | 0.00 | 0.00 | 0.00 | 0.00 | 0.00 | 0.00 |
| Isodecane | 0.00 | 0.00 | 0.00 | 0.00 | 0.00 | 0.00 | 0.00 | 0.00 | 0.00 | 0.00 | 0.00 |
| Histidine | 0.00 | 0.00 | 0.00 | 0.00 | 0.00 | 0.00 | 0.00 | 0.00 | 0.00 | 0.05 | 0.05 |
| Niacinamide | 0.00 | 0.00 | 0.00 | 0.00 | 0.00 | 0.00 | 0.00 | 0.00 | 0.00 | 0.50 | 0.50 |
| Caffeine | 0.00 | 0.00 | 0.00 | 0.00 | 0.00 | 0.00 | 0.00 | 0.00 | 0.00 | 0.10 | 0.10 |
| Panthenol | 0.00 | 0.00 | 0.00 | 0.00 | 0.00 | 0.00 | 0.00 | 0.00 | 0.00 | 0.89 | 0.89 |
| Benzyl Alcohol | 0.00 | 0.00 | 0.00 | 0.00 | 0.00 | 0.00 | 0.00 | 0.00 | 0.00 | 0.00 | 0.00 |
| Isostearyl Isostearate | 0.00 | 0.00 | 0.00 | 0.00 | 0.00 | 0.00 | 0.00 | 0.00 | 0.00 | 0.00 | 0.00 |
| Combing Force(gf)1 | | | | | | | | | | | |
| Combing Force(gf)2 | 53 | 176 | 42 | 142 | 66 | 268 | 76 | 128 | 246 | | |

| | Ex 23 | Ex 24 | Ex 25 | Ex 26 | Ex 27 | Ex 28 | Ex 29 | Ex 30 | Ex 31 | Ex 32 | Ex 33 |
|---|---|---|---|---|---|---|---|---|---|---|---|
| Water | 44.64 | 44.64 | 68.46 | 96.67 | 97.21 | 94.10 | 94.64 | 96.67 | 97.21 | 96.67 | 94.64 |
| Ethanol | 48.75 | 48.75 | 0.00 | 0.00 | 0.00 | 0.00 | 0.00 | 0.00 | 0.00 | 0.00 | 0.00 |
| Glycerol alpha-monooleate | 0.71 | 1.25 | 0.00 | 0.00 | 0.00 | 0.00 | 0.00 | 0.00 | 0.00 | 0.00 | 0.00 |
| Palmitoleic Acid | 0.00 | 0.00 | 0.00 | 0.00 | 0.00 | 0.00 | 0.00 | 0.00 | 0.00 | 0.00 | 0.00 |
| Ethylene glycol-monooleate | 0.00 | 0.00 | 0.00 | 0.00 | 0.00 | 0.00 | 0.00 | 0.00 | 0.00 | 0.00 | 0.00 |
| Oleic acid | 1.79 | 1.25 | 0.00 | 1.79 | 1.25 | 1.79 | 1.25 | 1.79 | 1.25 | 1.79 | 1.25 |
| Oleyl Alcohol | 0.00 | 0.00 | 0.00 | 0.00 | 0.00 | 0.00 | 0.00 | 0.00 | 0.00 | 0.00 | 0.00 |
| 2-Heptenoic acid | 0.00 | 0.00 | 0.00 | 0.00 | 0.00 | 0.00 | 0.00 | 0.00 | 0.00 | 0.00 | 0.00 |
| 2-Hexadecenoic acid | 0.00 | 0.00 | 0.00 | 0.00 | 0.00 | 0.00 | 0.00 | 0.00 | 0.00 | 0.00 | 0.00 |
| Methyl Oleate | 0.00 | 0.00 | 0.00 | 0.00 | 0.00 | 0.00 | 0.00 | 0.00 | 0.00 | 0.00 | 0.00 |
| DiisopropylAdipate | 0.00 | 0.00 | 25.00 | 0.00 | 0.00 | 0.00 | 0.00 | 0.00 | 0.00 | 0.00 | 0.00 |
| Isodecane | 0.00 | 0.00 | 5.00 | 0.00 | 0.00 | 0.00 | 0.00 | 0.00 | 0.00 | 0.00 | 0.00 |
| Histidine | 0.01 | 0.01 | 0.05 | 0.05 | 0.05 | 0.01 | 0.01 | 0.05 | 0.05 | 0.05 | 0.01 |
| Niacinamide | 2.50 | 2.50 | 0.50 | 0.50 | 0.50 | 2.50 | 2.50 | 0.50 | 0.50 | 0.50 | 2.50 |
| Caffeine | 1.00 | 1.00 | 0.10 | 0.10 | 0.10 | 1.00 | 1.00 | 0.10 | 0.10 | 0.10 | 1.00 |
| Panthenol | 0.60 | 0.60 | 0.89 | 0.89 | 0.89 | 0.60 | 0.60 | 0.89 | 0.89 | 0.89 | 0.60 |

TABLE 6-continued

| | | | | | | | | | | | |
|---|---|---|---|---|---|---|---|---|---|---|---|
| Benzyl Alcohol | 0.00 | 0.00 | 0.00 | 0.71 | 1.25 | 0.71 | 1.25 | 0.00 | 0.00 | 0.00 | 0.00 |
| Isostearyl Isostearate | 0.00 | 0.00 | 0.00 | 0.00 | 0.00 | 0.00 | 0.00 | 0.71 | 1.25 | 0.71 | 1.25 |
| Combing Force(gf)1 | | | | | | | | | | | |
| Combing Force(gf)2 | | | | | | | | | | | |

[1] Monomuls 90-O-18 supplied by BASF
[2] Supplied by Sigma Aldrich
[3] Greenolene 6928 supplied by Green Oleo
[4] Supplied by Ajinomoto
[5] Supplied by USP: Edison
[6] Supplied by DSM Nutritional Products
[7] Supplied by Roche
[8] Supplied by Incos Maastricht BV (Maastricht, NL)
[9] Isostearyl isostearate Crodamol ISIS supplied by Croda

TABLE 7

Aerosol Dry Conditioner Systems

| Description | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|
| Alcohol | 42.58% | 25.00% | 25.00% | 25.00% | 25.00% | 50.00% | 56.11% | 46.88% | 28.29% |
| Dry Flo Tapioca | 0.50% | | | | | | 2.00% | | |
| Cyclopentasiloxane | 0.50% | 5.63% | 5.63% | 5.63% | | 1.67% | | 10.00% | 5.00% |
| Hexamethyldisloxane | | 10.88% | 10.42% | 8.17% | 4.00% | 15.00% | | 10.00% | 15.00% |
| Dimethicone | | 2.25% | 2.25% | 4.50% | 0.50% | 6.75% | | 1.50% | 1.00% |
| Phenyl Trimethicone | 0.50% | | | | | | 1.00% | | |
| Cetrimonium Chloride | 0.20% | 0.20% | 0.20% | 0.20% | 0.20% | 0.10% | 0.40% | 0.30% | |
| Oleic Acid | 0.10% | 0.32% | 0.64% | 0.64% | 0.10% | 0.96% | 0.10% | 0.64% | 0.32% |
| Glyceryl Monoleate (GMO) | 0.04% | 0.14% | 0.28% | 0.28% | 0.04% | 0.42% | 0.04% | 0.28% | 0.14% |
| Caffeine | 0.05% | 0.05% | 0.05% | 0.05% | | | | | |
| Niacinamide | 0.50% | 0.50% | 0.50% | 0.50% | | | | | |
| Histidine | 0.01% | 0.01% | 0.01% | 0.01% | | | | | |
| Perfume | 0.02% | 0.02% | 0.02% | 0.02% | 0.16% | 0.10% | 0.35% | 0.40% | 0.25% |
| Dimethyl Ether | | | | | | | | 30.00% | |
| Hydrofluorocarbon 152a | | | | | | | | | 50.00% |
| Hydrocarbon Propellant | 55.00% | 55.00% | 55.00% | 55.00% | 70.00% | 25.00% | 40.00% | | |

Order of Addition:
Concentrate: Alcohol, GMO, Oleic Acid, Hexamethyldisiloxane, Dimethicone, Cyclopentasiloxane, Cetrimonium Chloride, Perfume, minors
Finished Product: 45% Concentrate, 55% Propellant The GMO is added directly after the alcohol to ensure that it goes into solution. There are no critical transformations with the concentrate formula.

In an embodiment, a method of hair treatment may be provided using a composition comprising a lipid and a lipid enhancing agent wherein the treated hair exhibits reduced combing force (gf) compared to untreated hair. The methods of hair treatment may be in the form of a leave on treatment.

It is further noted that terms like "alternatively," "usually", "generally," "commonly," and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is additionally noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method to improve softness of hair comprising:
   a) providing an aerosol container containing an aerosol dry conditioner system comprising:
      i) about 25% to about 70% liquefied propellant;
      ii) about 0.1% to about 0.96% oleic acid;
      iii) about 0.04% to about 0.42% glycerol monooleate;
      iv) about 10 wt. % to about 75 wt. % non-aqueous volatile solvent,
      wherein a weight ratio of oleic acid to glycerol monooleate is about 1:1 to about 2.5:1;
   b) identifying a hair tip that is damaged due to loss of lipids, wherein the hair tip comprises a lipid layer;
   c) applying the dry conditioner composition to the hair tip; and
   d) allowing the dry conditioner composition to remain on the hair tip so the glycerol monooleate enhances penetration of the oleic acid into the hair tip and the oleic acid is incorporated into the lipid layer thereby replenishing the lipid layer and improving hair softness.

2. The method of claim 1, wherein aerosol dry conditioner system comprises from about 0.1% to about 0.32% oleic acid.

3. The method of claim 1, wherein the aerosol dry conditioner system comprises from about 0.04% to about 0.14% glycerol monooleate.

4. The method of claim 1, wherein the aerosol dry conditioner system further comprises from about 15% to about 50% of a silicone selected from hexamethyldisiloxane, cyclopentasiloxane, dimethicone fluids, phenyl trimethicone, and mixtures thereof.

5. The method of claim 1, wherein the aerosol dry conditioner system further comprises one or more materials selected from niacinamide, caffeine, histidine, and mixtures thereof.

6. The method of claim 1, wherein the aerosol dry conditioner system further comprises a cationic surfactant system.

7. The method of claim 1, wherein the aerosol dry conditioner system comprises less than 0.1 wt. % water.

8. The method of claim 1, wherein the liquefied propellant wherein is selected from hydrocarbon blends, dimethyl ethers, hydrofluorocarbon 152a, and mixtures thereof.

9. The method of claim 1, wherein the non-aqueous volatile solvent is ethanol.

10. A method to improve softness of hair comprising:
    a) providing an aerosol container containing an aerosol dry conditioner system comprising:
       i) about 25% to about 70% liquefied propellant;
       ii) about 0.1% to about 0.96% oleic acid;
       iii) about 0.04% to about 0.42% glycerol monooleate;
       iv) about 10 wt. % to about 75 wt. % ethanol;
       v) 0.01% to about 50% of a silicone;
       vi) a perfume;
       wherein a weight ratio of oleic acid to glycerol monooleate is about 1:1 to about 2.5:1;
    b) identifying a hair tip that is damaged due to loss of lipids, wherein the hair tip comprises a lipid layer
    c) applying the dry conditioner composition to the hair tip comprising a lipid layer; wherein the dry conditioner composition comprises:
    d) allowing the dry conditioner composition to remain on the hair so the glycerol monooleate enhances penetration of the oleic acid into the hair and the oleic acid is incorporated into the lipid layer thereby replenishing the lipid layer and improving hair softness.

11. The method of claim 10, wherein the weight ratio of oleic acid to glycerol monooleate is from about 2:1 to about 3:1.

12. The method of claim 10, wherein the weight ratio of oleic acid to glycerol monooleate is from about 1:1 to about 2.5:1.

13. The method of claim 10, wherein the silicone comprises hexamethyldisiloxane.

14. The method of claim 10, wherein the silicone further comprises dimethicone.

15. The method of claim 10, wherein the aerosol dry conditioner system comprises about 15 wt. % to about 50 wt. % silicone.

16. The method of claim 10, wherein the active ingredients consist of oleic acid, glycerol monooleate, and silicone.

17. The method of claim 10, wherein the propellant is selected from propane, n-butane, isobutane, and mixtures thereof.

* * * * *